ies Patent [19]

[11] Patent Number: 5,045,549

Sauter et al.

[45] Date of Patent: Sep. 3, 1991

[54] SUBSTITUTED 4-PYRIDONE 3-CARBOXYLIC ACID DERIVATIVES, METHOD FOR THEIR PRODUCTION AND THEIR PHARMACEUTICAL COMPOSITIONS

[75] Inventors: Fritz Sauter; Ulrich Jordis; Manfred Rudolf, all of Vienna; Josef Wieser; Karl Baumann, both of Linz, all of Austria

[73] Assignee: Chemie Linz Gesellschaft m.b.H., Linz, Austria

[21] Appl. No.: 70,351

[22] Filed: Jul. 6, 1987

[30] Foreign Application Priority Data

Jul. 4, 1986 [DE] Fed. Rep. of Germany ....... 3622509

[51] Int. Cl.$^5$ .................... A61K 31/47; C07D 471/04; C07D 513/04
[52] U.S. Cl. .................... 514/312; 514/249; 514/291; 544/349; 546/80; 546/156
[58] Field of Search ................ 544/349; 546/156; 514/249, 312

[56] References Cited

U.S. PATENT DOCUMENTS

| 4,292,317 | 9/1981 | Pesson | 546/156 |
|---|---|---|---|
| 4,499,091 | 2/1985 | Wentland et al. | 546/156 |
| 4,571,396 | 2/1986 | Hutt et al. | 514/249 |
| 4,578,473 | 3/1986 | Domagala et al. | 546/156 |
| 4,730,000 | 3/1988 | Chu | 514/254 |
| 4,775,668 | 10/1988 | Jefson et al. | 546/156 |
| 4,851,418 | 7/1989 | Sanchez | 546/156 |
| 4,861,779 | 8/1989 | Jefson et al. | 514/312 |
| 4,920,120 | 4/1990 | Domagala et al. | 514/249 |
| 4,923,879 | 5/1990 | Hutt, Jr. et al. | 546/156 |
| 4,962,108 | 10/1990 | Hutt, Jr. et al. | 514/300 |
| 4,962,112 | 10/1990 | Rosen et al. | 546/156 |

FOREIGN PATENT DOCUMENTS

| 0131839 | 1/1985 | European Pat. Off. |
| 0159174 | 10/1985 | European Pat. Off. |
| 0215650 | 3/1987 | European Pat. Off. |
| 3601567 | 7/1987 | Fed. Rep. of Germany |

OTHER PUBLICATIONS

Rosen et al., "The Design, Synthesis and Properties of A-65485 and Related Quinolone Antibacterial Agents", Abstract of the 1987 ICAAC (10/1987).

*Primary Examiner*—Mukund J. Shah
*Assistant Examiner*—E. Bernhardt
*Attorney, Agent, or Firm*—Wenderoth, Lind & Ponack

[57] ABSTRACT

New 4-Pyridone derivatives of General Formula are claimed

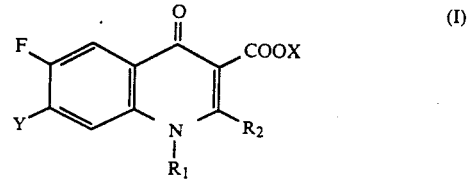

in which $R_1$ is methylamino,4-fluorophenyl, 2,4-difluorophenyl, $R_2$ is hydrogen or a sulfur atom that is joined to the ring nitrogen by an ethylene bride, X is a hydrogen or a physiologically removable ester group and Y is a base of the general formula

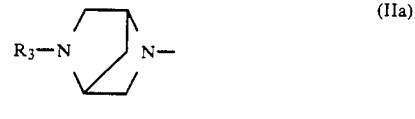

or

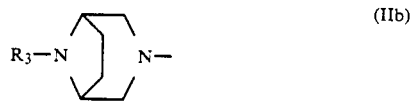

In formula IIa and IIb, $R_3$ is hydrogen, lower alkyl, benzyl, formyl, acetonyl or a moiety of the formula

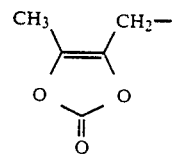

Also claimed are the addition salts of compounds of formula I with pharmaceutically acceptable inorganic or organic acids or base and/or their hydrates. Also claimed are the methods of manufacture of compounds of formula I and their use as antibacterial agents.

6 Claims, No Drawings

SUBSTITUTED 4-PYRIDONE 3-CARBOXYLIC ACID DERIVATIVES, METHOD FOR THEIR PRODUCTION AND THEIR PHARMACEUTICAL COMPOSITIONS

The invention concerns new 4-pyridone derivatives, the method for their manufacture, the pharmaceutical compositions which contain these substances, and their use as agents in the treatment of bacterial infections.

4-Pyridone derivatives, especially oxo derivatives of substituted quinoline, naphthyridine, benzoxazine and benzoquinoline carboxylic acids are known to have antibacterial activity. From this class of compounds, quinolone 3-carboxylic acids are described in U. S. Pat. No. 4,146,719, which in particular show a cyclic nitrogen base in the 7-position of the quinolone and these possess antibacterial activity.

In EP 131839 the antibacterial properties of quinoline carboxylic acid derivatives are described. These derivatives could be substituted in the 1-position with a p-fluorophenyl group and the characteristic substituent in the 7-position could be an aliphatic heterocylcic ring. Bridged, bicyclic nitrogen bases were however, not disclosed.

Finally EP-A-159174 reports oxo derivatives of substituted quinoline, naphthyridine and benzoxazine carboxylic acids which bera, as characteristic substitution in the 7-position of the quinolone or naphthyridone ring or in the 10-position of the benzoxazine ring, a bridged, bicyclic nitrogen base and these likewise have antibacterial activity.

Despite the large numbers of antibacterially active 4-pyridone derivatives reported in the literature, a need still exists for new compounds from this substance class, the known 4-pyridone derivatives. This need includes better activity and/or improved activity against certain types of bacterial infection, better stability, better pharmacokinetic properties and/or a better toxic side effects profile.

We have now discovered new oxo derivatives of quinoline, naphthyridine and benzoxazine carboxylic acids substituted with selected bridged nitrogen bases and which demonstrate interesting pharmacologic activity.

The scope of the invention is the new bridged nitrogen based substituted quinoline and benzoxazine carboxylic acids substituted by bridged nitrogen bases which possess interesting pharmacological properties.

In this view, the following discovery is new 4-pyridone derivatives of formula I from the structure Table.

$R_1$ is methylamino, 4-fluorophenyl and 2,4-difluorophenyl $R_2$ is hydrogen or a sulfur atom that joins an ethylene bridge with the ring nitrogen.

X is hydrogen or a physiologically removable ester group

Y is a base of formula IIa or IIb from the structure Table $R_3$ is hydrogen, lower alkyl, benzyl, formyl, acetonyl or a moiety of formula III from the structure Table.

Also disclosed are addition salts of formula I with pharmaceutically acceptable inorganic or organic acids or bases and or their hydrates.

In the present invention, the definition of "lower alkyl" is a straight or branched saturated chain with 1–4 carbon atoms such as methyl, ethyl, propyl, isopropyl-butyl, isobutyl, sec-butyl or t-butyl. The definition of "physiologically removable ester group" embraces esters which enhance the absorption of the active substance, for example pivaloyloxymethyl or 1-acetoxyethyl esters.

From the compounds of formula 1 the following is preferred:

$R_1$ is 4-fluorophenyl or 2,4-difluorophenyl, Y is a base of formula II in which $R_3$ is hydrogen, methyl or formyl.

Especially preferred are:

6-fluoro-1-(4-fluorophenyl)-1,4-dihydro-7-[5-methyl-2,5-diazabicyclo-(2.2.1.)hept-2-yl]-4-oxoquinoline-3-carboxylic acid and 6-fluoro-1-(2,4-difluorophenyl)-1,4-dihydro-7-[5-methyl-2,5-diazabicyclo(2.2.1)hept-2-yl]-4-oxoquinoline-3-carboxylic acid 7-[2,5-diazabicyclo(2.2.1)hept-2-yl]-6-fluoro-1-(2,4-difluorophenyl)-1,4-dihydro-4-oxoquinoline-3-carboxylic acid.

The compounds of this invention, have optical centers and could be utilized as racemates or in the form of their optical isomers This invention embraces both the racemates and the optical isomers.

The compounds of this invention relating to formula I can be produced as follows:

a) compounds are obtained from compounds of formula IV (from the structure table) in which $R_1$ and $R_2$ have the same significance as for formula I, L is a leaving group, such as chloro or fluoro,- and $R_4$ is hydrogen, lower alkyl or a boron complex -B($R_5R_6$) in which $R_5$ and $R_6$ each are fluoro or a moiety -O(CO)-lower alkyl, by reaction with a compound of the formula Va or Vb (from structure table) in which $R_3$ has the value signified in formula I or alternatively may be an amino protecting group.

b) The compounds of the claimed invention are also prepared from compounds obtained in Step a) in which $R_4$ is lower alkyl or a group -B($R_5R_6$) by removal of the group to produce a compound of formula I where X is hydrogen.

c) Compounds are prepared from compounds obtained in step a) or b) in which $R_3$ is an amino protecting group by removal of the group.

d) The compounds of general formula I, in which $R_3$ is a methyl-, a formyl-, or an acetonyl-, or a group of formula III are prepared from compounds of formula I, in which $R_3$ is hydrogen, by methylation, benzylation, formylation, or by reaction with bromoacetone or a material $R_7$-halogen, wherein $R_7$ is described by formula III.

e) The desired compounds of general formula I as their pharmaceutically acceptable addition salts are prepared by reaction with acids or bases and/or groups to prepare their physiologically removable esters.

In the reaction of compounds of Formula IV with compounds of formula V as outlined in process step a), one may use a base as the HX (acid) acceptor. An excess of the described base of general formula Va or Vb could be used. In general, one mole equivalent of a compound of general formula IV is reacted with 1–5 Mol of a compound of formula Va or Vb. The excess base of formula IV can be recovered through a workup of the mother liquor.

With the use of an equivalent amount of compounds of formula IV and the base of formula Va or Vb, an acid binding compound, such as 1,4-diazabicyclo(2.2.2)- octane, triethylamine or 1,8-diazabicyclo(5.4.0)undec-7-ene, is employed.

The reaction in step a) is conducted in solutions or mixtures as for example with dimethylsulfoxide, 1,3-dimethyltetrahydro-2-(1H)pyrimidone, hexamethylphosphoroustriamide, sulfolone, pyridine, Lutidine or collidine or in mixtures of the above solvents. It is also possible to employ as the solvent one of the above named bases or mixtures of these bases with one of the above named solvents.

The reaction time of a) is from 1 to 5 hours and the reaction temperature is 100° C.–200° C., with the range of 130° C. –170° C. being preferred.

In the event that the product does not precipitate with cooling and thus cannot be filtered off, the product is isolated by removal of the volatile constituents under vacuum conditions and subsequent isolation of the residue or of isolation as a resultant of preparation of one of its salts or through a combination of these actions.

In an especially preferred variation of reaction step a) the reactivity of such compounds as in general formula IV is increased by the formation of a mixed boronic anhydride or where $R_4$ is a moiety of the type $B(R_5R_6)$. The reaction time required when these boron complexes are used are between 1–30 hours with a temperature between ambient (room temperature) and 50° C.

In the reaction in a) of compounds of Formula Va or Vb and where $R_3$ is hydrogen, it is not necessary, but in many cases advantageous, that compounds of formula I have $R_6$ as an amino protecting group to guard against nucleophilic substitution at this position. A general list of groups is as follows:

An acyl group such as formyl, acetyl, trifluoroacetyl; an alkoxycarbonyl group such as ethoxycarbonyl, t-butoxycarbonyl, beta,beta,beta-trichloroethoxycarbonyl; aryloxycarbonyl groups such as benzyloxycarbonyl, phenoxycarbonyl; and groups such as trimethylsilyl, trityl, p-toluenesulfonyl and benzyl.

In the reaction step b) $R_4$, which is lower alkyl or -$B(R_5R_6)$ is removed by refluxing the product from a) with about a 10 fold excess of dilute sodium hydroxide solution. After cooling, the solution is neutralized with HCl, the resultant precipitate filtered off and after the usual methods such as washing and recrystallizations the product is isolated.

The removal of the amino protecting group in step c) can be done by known methods after the isolation of the product of formula I. Thus for example, the ethoxycarbonyl group is removed by hydrolysis in acidic or basic media or the trityl group can be removed by hydrogenation.

The methylation of compounds of formula I, in which $R_3$ is hydrogen, according to step d) can be performed for example with methyl iodide or dimethylsulfate or by refluxing of the secondary amine in a 10–20 fold excess of a mixture of formic acid and 40% formaldehyde solution for a period of 0.5 to 5 hr. The reaction product was after concentration dissolved in water, brought to pH 7 with dilute ammonia and extracted with a mixture of methylene chloride and chloroform. Removal of the volatile organic phase and recrystallization from methanol/ether gave the desired alkylated product.

The formation of compounds of Formula I in which $R_3$ is hydrogen is accomplished for example by reaction with a mixed formic acetic anhydride. The reaction with bromoacetone or a compound $R_7$-halogen can for example be conducted in an inert solvent such as dimethyformamide in the presence of an acid binder such as $KHCO_3$.

Finally in reaction step e) one generates after a) to d) the amphoteric compounds, their basic or acid addition salts or their physiologically removable esters. The salts are generated by bases, by reaction at the carboxylic acid group and the following are acceptable: alkali, alkali earth, ammonia and silver as well as the salts from the pharmaceutically acceptable bases as choline, diethanolamine, ethylendiamine, guanidine and others.

Salts were prepared from pharmaceutically acceptable inorganic or organic acids by reaction with the basic portion of the molecule Examples of such acids are hydrochloric acid, sulfuric acid, phosphoric acid, acetic acid, citric acid, oxalic acid, malonic acid, salicylic acid, methanesulfonic acid and others.

The synthesis of physiologically acceptable esters can be prepared by generally known methods The starting materials for the desired compounds of structural formula IV are known or could be prepared by analogous procedures. Methods for their preparation are described in EP47005, EP159174, EP203, EP78362, in J. Med. Chem., 1980, 23, 1358 in J. Med. Chem., 1985, 28, 1558, and also in J. Heterocycl. Chem. 1985, 22, 1033.

The intermediate 6,7-difluoro-1-(4-fluorophenyl)1,4-dihydro-4-oxoquinoline-3-carboxylic acid or 6,7-difluoro-1-[2,4-difluorophenyl)1,4-dihydro-4-oxoquinoline-3-carboxylic acid was prepared starting from acid chloride VI or halo variants. This was reacted with the magnesium salt of malonic acid monoethyl mono-t-butyl ester to give acylmalonyl ester VII which was converted to the aroylacetic acid ethyl ester VIII by reaction with trifluoroacetic acid. The condensation of VIII with triethyl ortho formate/acetic anhydride produced 2-(2-chlor-4,5-difluorobenzoyl)3-ethoxyacrylic acid ethyl ester IX. This was reacted with 4-fluoraniline (or 2,4-difluoraniline) to generate examine X which cyclized upon treated with sodium hydride to quinolone ester XI (R=ethyl) and this was hydrolyzed to the quinolone acid XI (R=1X).

The starting material for the synthesis of 2-chloro-4.5-difluorobenzoyl chloride VI was obtained from the corresponding acid and thionyl chloride. The 2-chloro-4,5-difluorobenzoic acid was obtained by a Sandmeyer-Reaction on 4,5-difluoroanthranilic acid in analogy to EP 55629.

The preparation of the boron complexes of compounds of the general formula IV is likewise known in the literature and is described in the Japanese Patent application 82/233684, 83/188138 and 85/126290.

The bases of the formula V are reported in the literature and are described in the following references or can be prepared by slight changes in the reported process.

1) P. A. Sturm, D. W. Henzy, P. E. Thompson, J. B. Zeigler and S. W. McCall, J. Med. Chem., 1978, 17, 481.
2) R. A. Barnes and H. M. Fales, J. Amer. Chem. Soc. 1953, 75, 975.
3) R. J. Michaels and H. E. Zaugg, J. Org. Chem. 1960, 25, 637.
4) H. Newman, J. Heterocycl. Chem. 1974, 11, 449.
5) P. S. Dortoghese and A. A. Mikhail, J. Org. Chem., 1966, 31, 1059.
6) P. C. Ruenitz and E. E. Smessman, J. Heterocycl. Chem., 1976, 13, 1111.

The compounds of this invention possess high antibacterial activity against a variety of pathogenic bacteria. For example, *E. Coli, Klebsiella, Enterobacter, Serratia, Acinetobacter, Pseudomonas, Staphylococcus, Streptococcus, Bacteroides, Clostridium* and *Peptococcus*.

The compounds of the invention are useful for treating bacterial infections in animals and humans, the use in humans being preferred. The antibacterial activity was measured by the MIC values (minimum inhibitory concentration) in vitro and also by the $ED_{50}$ values in vivo. The comparative substances were Ciprofloxacin (from EP 78362), pefloxacin (from DE-OS 2843066) and enoxacin (EP 9425). The superiority of the invention compounds was evident especially against gram positive bacteria and with oral application, the absorption of the invention compounds was significantly better.

The compounds of formula I could find use as medicants, and in the form of pharmaceutical preparations in which they are contained are suitable for oral or parenteral applications. These individual formulations may contain inert organic or inorganic carriers and/or binders as for example pharmaceutically acceptable solution media, such as gelatin, gum arabicum, milk sugar (lactose), starch, magnesium stearate, talk plant oil, polyalkyleneglycols, Vaseline and the like.

The pharmaceutical preparation can be in a solid form, and as a tablet, coated pill, suppositories, capsules and such; in a semisolid state such as salves or ointments or liquid form as in solutions, suspension or emulsions. If necessary, they can be sterilized and contain adjutants as preservatives, stabilizers or emulsifiers, salts to alter the osmotic pressure and the like. Also, pharmaceutical preparations of the invention compounds can be combined with other therapeutically valuable substances. The invention compounds could be formulated with these compounds together with the above named carriers, binders or diluents.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 30 mg per kilogram daily. A daily dose range of about 3 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples explain the invention.

EXAMPLE 1

1,4-dihydro-6-fluoro-methylamino-7-(8methyl-3,8-diazabicyclo (3.2.1) oct-3-yl)-4-oxoquinoline-3-carboxylic acid 0.42 g (1.60 m Mol) 7-Chloro-6-fluoro-1,4-dihydro-1-methylamino-4-oxoquinoline-3-carboxylic acid, 0.60 g (4.8 m Mol) 8-methyl-3,8-diazabicyclo(3.2.1.)octane and 1 ml dimethylsulfoxide was stirred at 140° C. for 3 hrs. After cooling, the deposited crystals were collected by filtration, washed with ether and crystallized from 2N hydrochloric acid. The hydrochloride of the compound was obtained as yellowish crystals, mp 291° C.-294° C. (dec.). Yield 0.25 g (43%).

EXAMPLE 2

1,2-Dihydro-7-fluoro-8-(8-methyl-3,8-diazabicyclo(3.2.1)oct-3-yl)-5-oxo-5H-thiazolo(3.2a)-quinoline-4-carboxylic acid 0.46 g (1.53 m Mol) 8-chloro-1,2-dihydro-7-fluoro-5-oxo-5H-thiazolo(3.2a)quinoline-4-carboxylic acid, 0.57 g (4.52 m Mol) 8-methyl-3,8-diazabicyclo(3.2.1)octane and 4.0 ml of dimethylsulfoxide was stirred at 140° C. for 2 hrs. After 30 mins., the reaction components dissolved, later however, the mixture became turbid. After cooling the product was filtered off washed with dimethylsulfoxide, methanol and then ether. Recrystallization from DMF gave 0.32 g (54%) of light yellow crystals, mp 308° C.-311° C. dec.

EXAMPLE 3

8-(2,5-Diazabicyclo(2.2.1)hept-2-yl)-1,2-dihydro-7-fluoro-5-oxo-5H-thiazolo(3.2a)quinoline-4-carboxylic Acid Dihydrochloride As described in example 2, 0.42 g (1.40 m Mol) 8-chloro-1,2-dihydro-7-fluoro-5-oxo-5H-thiazolo(3.2a)-quinoline-4-carboxylic acid and 0.28 g (2.85 m Mol) 2,5diazabicyclo(2.2.1)heptane were reacted. After recrystallization from dimethylformamide with activated carbon, the compound was treated with dicyclohexylamine in acetone and with 2N hydrochloric acid to give 0.24 g (28%) of the product as the dihydrochloride containing 1 mol. equivalent of dicyclohexylamino, mp >150° C. dec.

EXAMPLE 4

6-Fluoro-1-(4-fluorophenyl)-1,4-dihydro-7(8-methyl-3,8-diazabicyclo(3.2.1)oct-3-yl)-4-oxoquinoline-3-carboxylic acid 0.5 g (1.4 m Mol) of 6,7-difluoro-1-(4-fluorophenyl)1,4-dihydro-4-oxoquinoline-3-carboxylic anhydride with difluorboronic acid (prepared by heating 6,7-difluoro-1(4-fluorophenyl)-1,4-dihydro-4-oxoquinoline-3-carboxylic acid with distilled boron trifluoride-etherate-following D. T. W. Chu, et al., J. Med. Chem, 1985, 28, 1558) and 0.4 g (2.0 m Mol) 8-methyl-3,8-diazabicyclo(3.2.1)octane dihydrochloride in 20 ml of absolute dimethylsulfoxide and 0.60 g (6.0 m Mol) triethylamine were heated at 40° C. for 24 hrs. The volatiles were removed under high vacuum and the residue refluxed for 1 hr. in 30 ml of 1 N NaOH. After treatment with active carbon, and filtration, the solution was treated with 2N HCl and the precipitate collected. After recrystallization from water/DMF, the product as the dihydrochloride was isolated as colorless crystals. Yield 0.28 g (40%) mp >280° dec.

EXAMPLE 5

6-Fluoro-1-(4-fluorophenyl)-1,4-dihydro-7(5-methyl-2,5-diazabicyclo(2.2.1)hept-2-yl)-4-oxoquinoline-4-carboxylic acid Analogous to the process in Example 4 but with 0.19 g (1.68 m Mol) of 2-methyl-2,5-diazabicyclo(2.2.1)heptane as the base starting material, 0.48 g (56%) of colorless crystals of the hydrochloride were obtained mp >265° C. dec.

EXAMPLE 6

6-Fluoro-1-(4-fluorophenyl)-1,4-dihydro-4-oxo-7-(5-benzyl-2,5-diazabicyclo(2.2.1)hept-2-yl)quinoline-3-carboxylic acid To a solution of 1.5 g (4 m Mol) of the mixed anhydride of 6,7-difluoro-1-(4-fluorophenyl)-1,4-dihydro-4-oxoquinoline-3-carboxylic acid with difluoroboronic acid in 10 ml of dimethylsulfoxide was added 0.9 g (4.78 m Mol) 2-benzyl-2.5-diazabicyclo(2.2.1)heptane and 0.4 g (4 m Mol) of triethylamine. After stirring for 4 hrs at room temperature, 150 ml of ether was added and the crystals that formed were collected by filtration. The residue was heated in a mixture of 60 ml dioxane and 90 ml 1.5N NaOH and heated at 100° C. for 1 hr. The hot solution was filtered to removed non-dissolved material. The solution was neutralized with conc HCl and the resultant crystals collected, washed with water and left to dry in the air. After recrystallization from DMF, 1.23 g (63%) of the product was obtained, mp 275°-280° dec.

EXAMPLE 7

7-(2,5-diazabicyclo-(2.2.1)hept-2-yl)-6-fluoro-1-(4-fluorophenyl-1,4-dihydro-4-oxoquinoline-3carboxylic acid 7.07 g (2.2 m Mol) 6-Fluoro-1-(4-fluorophenyl)-1,4-dihydro-4-oxo-7-(2-benzyl)-2,5-diazabicyclo(2.2.1)-hept-2-yl)quinoline-3-carboxylic acid was dissolved in 70 ml absolute ethanol containing 7 g HCl. 1 g of pulverized 10% Pd/c was added and the mixture placed in a hydrogenation apparatus and maintained at 15 psi $H_2$ and 60° C. for 90 min. The mixture was filtered to remove the catalyst and the volatiles removed on a rotary evaporator. The residue was dissolved in 30 ml of 1 N NaOH solution and the slightly turbid solution filtered. The solution was neutralized by the addition of conc HCl. 50 ml of DMF was added and the solution heated to 100° until most of the solid had dissolved. After filtration and cooling 0.68 g (74.4%) of crystalline monohydrate was obtained, mp 290° C.-309° C. dec.

EXAMPLE 8

7-(5-formyl-2,5-diazabicyclo(2.2.1)hept-2vl)6-fluoro-1-(4-fluorophenyl)-1,4-dihydro-4-oxoquinoline-3carboxylic acid To 1.2 g (3 m Mol) 7-(2,5-diazabicyclo(2.2.1)hept-2-yl)-6-fluoro-1-(4-fluorophenyl)1,4-dihydro-4-oxoquinoline-3-carboxylic acid in 10 ml of formic acid was added 2.64 g (30 m Mol) of the mixed anhydride of acetic and formic acids and the mixture was stirred for 6 hrs. The volatiles were removed in vacuo and the residue recrystallized to give 0.4 g (31%) of the product, mp 274° C.-276° C.

EXAMPLE 9

6-Fluoro-1-(2,4-difluorophenyl)-1,4-dihydro7-(5-methyl-2,5-diazabicyclo(2.2.1)hept-2-yl)-4-oxoquinoline-3-carboxylic acid 15 g (37.36 m Mol) of the mixed anhydride of 7-chloro-6-fluoro-1-(2,4-difluorophenyl)-1,4-dihydro-4-oxoquinoline-3-carboxylic acid and difluoroboronic acid (obtained by heating 7-chloro-6-fluoro-1-(2,4-difluoro- phenyl)-1,4-dihycho-4-oxoquinoline-3-carboxylic acid in 60% aqueous fluoroboronic acid 15.36 g (56 m Mol) of the dihydrobromide of 2-methyl-2,5-diazabicyclo-(2.2.1)heptane and 31 ml (0.224 mol) triethylamine was stirred in 200 ml of dry DMSO at room temperature for 6 days. Then the reaction mixture was poured into 800 ml of cold water and the resultant precipitate collected by filtration washed with water and then heated to reflux with stirring in a mixture of 100 ml dioxane and 150 ml 3N NaOH for 1 hr. After cooling and with stirring, 500 ml of conc. HCl was added. After stirring for 1 hr., the undissolved material was removed by filtration, to give a clear solution which was extracted multiple times with methylene chloride. The aqueous phase was cooled in an ice bath and brought to pH 7.4 by the addition of dilute NaOH. The resultant was extracted with chloroform and the chloroform phase dried over sodium sulfate and the chloroform removed in vacuo, the resulting dark brown oil was recrystallized from 450 ml ethanol to give 3.15 g (18.8%) of the product as a hydrate, mp 215° C.-220° C. dec.

EXAMPLE 10

6-Fluoro-1-(2,4-difluorophenyl)1,4-dihydro4-oxo-7-(5-benyl-2,5-diazabicyclo(2.2.1)-hept-2-yl)-quinoline-3-carboxylic acid Analogous to example 6 but utilizing 5.56 g (13.85 m Mol) of the mixed anhydride of 7-chloro-6-fluoro-1-(2,4-difluorophenyl)1,4-dihydro-4-oxoquinoline-3-carboxylic acid and difluoroboronic acid, 5.82 g (16.62 m Mol) 2-benzyl-2,5-diazabicyclo(2.2.1)heptane dihydrobromide and 11.58 ml (83 m Mol)triethylamine in 50 ml dry DMSO yielded 2.73 g (39%) of the product, mp 233° C.-238° C. dec.

EXAMPLE 11

7-(2,5-diazabicyclo(2.2.1)hept-2-yl)-6-fluoro-1-(2,4-difluorophenyl)-1,4-dihydro-4-oxoquinoline3-carboxylic acid 2.57 g (5 08 m Mol) of 6-fluoro-1-(2,4-difluorophenyl)-1,4-dihydro-4-oxo-7-(5-benzyl-2,5-diazabicyclo(2.2.1)-hept-2-yl)quinoline-3-carboxylic acid was dissolved in 170 ml of absolute ethanol containing 18 g of HCl and to the solution was added 2.1 g 10% Pd/c and the resultant hydrogenated at 15 psi and 60° C. for 2 hrs. After filtration of the catalyst the volatiles were removed under reduced pressure. The resulting residue was taken up in 80 ml of water and the pH adjusted to 7. The resulting suspension was heated for 20 mins. at 60° C. After cooling the precipitated was filtered and recrystallized from DMF to give 1.53 g (69.5%) of product as a hydrate, mp 198° C.-204° C. dec.

EXAMPLE 12

7-(5-Formyl-2,5-diazabicyclo-(2.2.1)hept-2-yl)-6-fluoro-1-(2,4-difluorophenyl)-1,4-dihydro-4-oxoquinoline-3-carboxylic acid 0.5 g (1.2 m Mol) 7-(2,5-diazabicyclo(2.2.1)hept-2-yl)-6-fluoro-1-(2,4-difluorophenyl)-1,4-dihydro-4-oxo-quinoline-3-carboxylic acid was suspended in 20 ml DMF and treated with 3 ml of the mixed anhydride of acetic and formic acid. After 90 mins. stirring at room temperature the volatiles were removed under reduced pressure. The oily residue was triturated with ether, the residue filtered and recrystallized from a mixture of 20 ml DMF and 5 ml ligroin to give 0.24 g (45.3%) of product, mp 252° C.-258° C. dec.

EXAMPLE 13

7-[5-Acetonyl-2,5-diazabicyclo(2.2.1)hept-2yl]-6-fluoro-1-(4-fluorophenyl)-1,4-dihydro-4-oxo-3-quinoline carboxylic To a solution of 0.6 g (1.5 m Mol) of 7-[(2,5-diazabicyclo(2.2.1)hept-2-yl)]-6-fluoro-1-(4-fluorophenyl)-1,4-dihydro-4-oxo-3-quinoline carboxylic acid in 60 ml of dimethylformamide was added 0.23 g (1.65 m Mol) calcium carbonate and 0.82 g (6 m Mol) bromoacetone and the reaction mixture stirred at room temperature for 6 hrs. The unreacted bromoacetone and the dimethylformamide were removed under reduced pressure and the residue was dissolved in 1N NaOH, filtered and the pH of the filtrate adjusted to 6.5 with 4N hydrochloric acid. The resulting precipitate was collected by filtration dissolved in methanol and chromatographed on silica gel (Elution with 5:4 benzene/methanol). Obtained was 0.20 g (29.4$) of product, mp 200° C.-205° C. dec.

EXAMPLE 14

1-(2,4-difluorophenyl)-6-fluoro-1,4-dihydro7-(5((5-methyl-2-oxo-1,3-dioxolen-4-yl)methyl)-2,5diazabicyclo(2.2.1)-hept-2-yl)-4-oxoquinoline-3-carboxylic acid To 188 mg (0.434 m Mol) of 7-(2,5-diazabicyclo(2.2.1-)hept-2-yl)-6-fluoro-1-(2,4-difluorophenyl)-1,4-dihydro-4-oxoquinoline-3-carboxylic acid monohydrate (Example 11) was suspended in 20 ml dry DMF was added 96 mg (0.95 m Mol) anhydrous calcium bicarbonate and 92 mg (0.48 m Mol) 4-bromomethyl-5-methyl-1,3-dioxolen-2-one. The resultant suspension was stirred at room temperature for 10 hrs. Then the suspension was treated with 150 ml of ethyl acetate and 50 ml of water. The organic phase was separated and washed with 5×30 ml water, dried over sodium sulfate, filtered the volatiles were removed at room temperature under reduced pressure. Recrystallization from ethyl acetate gave 63 mg (27.5%) of the desired material.

EXAMPLE A

DETERMINATION OF THE IN VITRO ANTIBACTERIAL ACTIVITY

The antibacterial activity of the compound of example 5 (Compound 5) was determined in the MIC test (minimum inhibitory concentration) in an Agar dilution assay against a variety of gram-positive and anaerobic bacteria using ciprofloxacin and pefloxacin or enoxacin as the standard. The results are summarized in Table 1.

TABLE 1

| Organism Gram Positive Bacteria | MIC (mcg/ml) for | | | | | |
|---|---|---|---|---|---|---|
| | 50% Inhibitious | | | 90% Inhibitious | | |
| (a) Gram positive Bacteria | Compd 5 | CF | PF | Compd 5 | CF | PF |
| Staphylococcus aureus MSSA | 0.25 | 0.5 | 0.5 | 0.5 | 1 | 1 |
| Staphylococcus aureus MRSA | 0.25 | 1 | 0.5 | 1 | 1 | 1 |
| Streptococcus beta-hemolytic | 1 | 0.5 | 4 | 4 | 1 | 8 |
| Streptococcus pneumoniae | 1 | 1 | 4 | 2 | 2 | 8 |
| Streptococcus faecalis | 4 | 1 | 4 | 8 | 2 | 8 |
| (b) anaerobe bacteria | Compd | CF | EC | Compd | CF | EC |
| Bacteroides fragilis | 4 | 4 | 16 | 4 | 4 | 16 |
| Bacteroides app. | 8 | 16 | 16 | 8 | 16 | n.t. |

Compound of Example 5
CF: Ciprofloxacin
PF: Pefloxacin
EC: Enoxacin
N.T.: Not tested

EXAMPLE B

DETERMINATION OF THE IN VITRO ANTIBACTERIAL ACTIVITY

The in vivo antibacterial activity of the compound of example 5 (compound 5) was performed in mice against an acute lethal infection in comparison with ciprofloxacin and pefloxacin. In this test, white mice (weight 20±2 g) of Charles River strain CDI received an intraperitoneal injection of a specific amount of a suspension of a bacterial cell culture. The amount is sufficient to cause death of untreated animals within 24-48 hrs. A half hour later, the test animals were administered either an oral or a subcutaneous dosing of the test compound in 0.5 ml of 0.2% starch solution. With streptococcal infections, the test animals received a second dose after 3 hrs. Each test group had 5 animals and each test was performed three times. The $ED_{50}$ values were calculated on the basis of the survivors at 7 days. An estimate of the oral absorption of the test compounds was determined from the ratio of the $ED_{50}$ values from the oral and subcutaneous dosings.

TABLE I

| Infection | Dosing | Ratio | $ED_{50}$ mg/kg/Dose | | |
|---|---|---|---|---|---|
| | | | Cmpd. 5 | CF | PF |
| Escherichia coli 314 | oral | | 0.96 | 0.52 | 0.84 |
| | s.c. | | 0.67 | 0.07 | 0.48 |
| | | o/s | 1.4 | 7.4 | 1.7 |
| Klebsiella pneum. AD | oral | | 0.65 | 0.38 | 0.80 |
| | s.c. | | 0.54 | 0.07 | 0.71 |
| | | o/s | 1.1 | 4.8 | 1.1 |
| Staph. aureus Smith | oral | | 1.1 | 4.3 | 3.8 |
| | s.c. | | 0.56 | 0.64 | 1.4 |
| | | o/s | 2 | 6.7 | 2.7 |
| Staph. aureus SSC-80-32 | oral | | 0.75 | 5.9 | n.t. |
| | s.c. | | 0.46 | 0.71 | n.t. |
| | | o/s | 1.6 | 8.3 | |
| Strept. pneum. SVI | oral | | 20 | 47 | n.t. |
| | s.c. | | 45 | 15 | n.t. |
| | | o/s | 0.44 | 3.1 | |
| Strept. pyogenes C 203 | oral | | 5.4 | 21 | n.t. |
| | s.c. | | 6.2 | 4 | n.t. |
| | | o/s | 0.87 | 5.3 | | oral: dosing
s.c.: subcutaneous dosing
Cmpd 5: Compound from example 5
CF: Ciprofloxacin
PF: Pefloxacin
n.t.: not tested
Ratio o/s: Ratio of the $ED_{50}$ values from oral and subcutaneous administration.

EXAMPLE C

DETERMINATION OF THE IN VITRO ANTIBACTERIAL ACTIVITY

The antibacterial activity of compounds of example 9 and 11 were determined in the MIC test (Agar dilution assay, Miller-Hinton Media) against various gram negative and gram-positive bacteria with pefloxacin as the standard. The results are summarized in Table III.

TABLE III
MICROBIOLOGY RESEARCH DEPARTMENT
IN VITRO ANTIBACTERIAL ACTIVITY

TEST: 406  
MEDIUM: MUEL-HIN  
INCUBATION: 18 Hrs. 35 Celsius  
METHOD: AGAR DIL  
INOCULUM: 1.0E+04 - 5.0E+04  
Aerobic: T

| | CL NUMBER NOTEBOOK - PAGE | | | MINIMAL INHIBITORY CONC., mcg/ml | | |
|---|---|---|---|---|---|---|
| ORGANISM | SRCE | YR | NO. | PF | Cmpd. 9 | Cmpd. 11 |
| 1 ESCH COLI | MOR | 84 | 20 | 0.060 | 0.015 | 0.008 |
| 2 ESCH COLI | VGH | 84 | 19 | 0.060 | 0.015 | 0.008 |
| 3 ESCH COLI | CMC | 84 | 50 | 0.060 | 0.060 | 0.030 |
| 4 KLEB PNEUM | CMC | 84 | 31 | 0.120 | 0.060 | 0.030 |
| 5 KLEB PNEUM | MOR | 84 | 24 | 0.120 | 0.060 | 0.060 |
| 6 KLEB PNEUM | IO | 83 | 5 | 0.250 | 0.120 | 0.060 |
| 7 ENTERO CLO | VGH | 84 | 39 | 0.120 | 0.060 | 0.030 |
| 8 ENTERO CLO | K | 84 | 10 | 0.060 | 0.030 | 0.015 |
| 9 ENTERO CLO | MOR | 84 | 30 | 0.250 | 0.060 | 0.030 |
| 10 SERRAT MARC | MOR | 84 | 41 | 0.060 | 0.120 | 0.060 |
| 11 SERRAT MARC | CMC | 83 | 74 | 4.000 | 4.000 | 4.000 |
| 12 SERRAT MARC | IO | 83 | 63 | 0.250 | 0.500 | 0.250 |
| 13 MORG MORG | VGH | 84 | 12 | 0.250 | 0.250 | 0.060 |
| 14 MORG MORG | CMC | 84 | 38 | 0.030 | 0.250 | 0.120 |
| 15 MORG MORG | MOR | 84 | 45 | 0.030 | 0.120 | 0.030 |
| 16 PROT RETT | IO | 83 | 21 | 0.120 | 0.060 | 0.030 |
| 17 PROV STUA | CMC | 83 | 3 | 4.000 | 4.000 | 2.000 |
| 18 CITRO DIV | K | 82 | 24 | 0.030 | 0.030 | 0.008 |
| 19 PSEU AERUG | K | 84 | 16 | 4.000 | 1.000 | 0.500 |
| 20 PSEU AERUG | VGH | 84 | 3 | 8.000 | 4.000 | 1.000 |
| 21 PSEU AERUG | CMC | 83 | 20 | 2.000 | 0.500 | 0.250 |
| 22 STAPH AUR | VGH | 84 | 47 | 0.250 | 0.030 | 0.250 |
| 23 STAPH AUR | K | 82 | 26 | 0.250 | 0.015 | 0.120 |
| 24 STAPH AUR | CMC | 83 | 131 | 2.000 | 0.500 | 0.250 |
| 25 STREP FAEC | UCI | 85 | 30 | 4.000 | 0.500 | 0.500 |
| 26 STREP FAEC | VGH | 84 | 69 | 2.000 | 0.500 | 0.500 |
| 27 STREP FAEC | CMC | 83 | 120 | 4.000 | 0.500 | 0.500 |
| 28 ESCH COLI | ATCC | 0 | 25922 | 0.030 | 0.030 | 0.008 |
| 29 STAPH AUR | ATCC | 0 | 29213 | 0.250 | 0.030 | 0.250 |

FORMULA TABLE

III.

IV.

FORMULA TABLE

I

IIa   IIb

Va   Vb

VI   VII

-continued
FORMULA TABLE

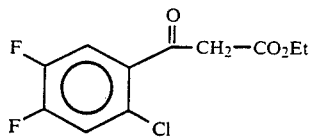

VIII

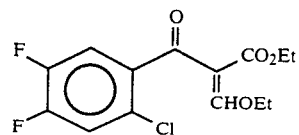

IX

FORMULA TABLE

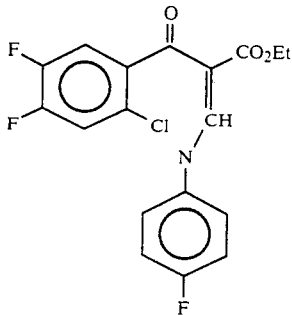

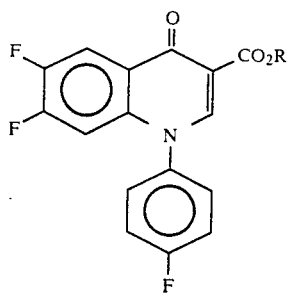

We claim:
1. A compound of the formula

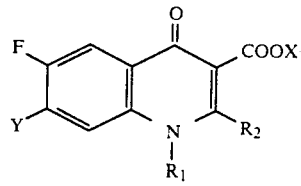

wherein
R₁ is 2,4-difluorophenyl,
R₂ is hydrogen,
X is hydrogen or a physiologically removable ester,
Y is a base of the formula

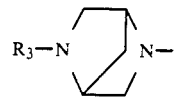

wherein R₃ is hydrogen, lower alkyl, benzyl, formyl, acetonyl or a moiety of the formula

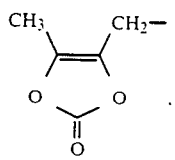

or a pharmaceutically acceptable acid addition salt thereof.
2. 6-fluoro-1-(2,4-difluorophenyl)-1,4-dihydro-7-(5-methyl-2,5-diazabicyclo-(2.2.1)hept-2-yl)-4-oxoquinoline-3-carboxylic acid.
3. 7-(2,5-diazabicyclo-(2.2.1)hept-2-yl)-6-fluoro-1-(2,4-difluorophenyl)-1,4-dihydro-4-oxoquinoline-3-carboxylic acid.
4. 6-fluoro-1-(2,4-difluorophenyl)-1,4-dihydro-7-(5-formyl-2,5-diazabicyclo)-(2.2.1)hept-2-61)-4-oxoquinoline-3-carboxylic acid.
5. An antibacterial composition which comprises an antibacterially effective amount of a compound or pharmaceutically acceptable salt thereof as defined in claim 1 and a pharmaceutically acceptable carrier thereof.
6. A method for the treatment or prophylaxis of bacterial infection which comprises administering to a patient an antibacterially effective amount of a compound or pharmaceutically acceptable salt thereof according to claim 1.

* * * * *